United States Patent [19]

Frank et al.

[11] Patent Number: 5,211,626

[45] Date of Patent: May 18, 1993

[54] MEDICAL INFUSION APPARATUS

[75] Inventors: Peter Frank, London; Terence G. Giles, Coulsdon, both of England

[73] Assignee: Product Innovation Holdings Ltd., Hertsfordshire, England

[21] Appl. No.: 627,906

[22] Filed: Dec. 17, 1990

Related U.S. Application Data

[63] Continuation of Ser. No. 188,504, Apr. 29, 1988, abandoned.

[30] Foreign Application Priority Data

May 1, 1987 [GB] United Kingdom ............... 8710441

[51] Int. Cl.$^5$ ........................ A61M 31/00; A61M 5/00
[52] U.S. Cl. ................................. 604/65; 604/122; 604/134; 604/246; 604/249; 604/250; 128/DIG. 12; 128/DIG. 13
[58] Field of Search ............ 604/65, 131, 134, 30, 604/67, 50, 113, 114, 246, 122, 249, 250; 128/DIG. 12, DIG. 13; 73/861.95, 861.91, 202.5, 204.11

[56] References Cited

U.S. PATENT DOCUMENTS

| | | | |
|---|---|---|---|
| 3,543,752 | 12/1970 | Hesse et al. ........................ | 128/214 |
| 3,647,117 | 3/1972 | Hargest ............................. | 604/134 |
| 3,670,926 | 6/1972 | Hill .................................. | 604/134 |
| 3,731,679 | 5/1973 | Wilhelmson et al. ............. | 128/214 F |
| 3,807,228 | 4/1974 | Matzuk ............................. | 73/194 E |
| 3,832,998 | 9/1974 | Gregg .............................. | 604/65 |
| 3,942,378 | 3/1976 | Olmstead ......................... | 73/204.19 |
| 4,228,683 | 10/1980 | Joffa et al. ....................... | 73/861.95 |
| 4,261,388 | 4/1981 | Shelton ............................ | 604/65 |
| 4,335,616 | 6/1982 | Oliva et al. ...................... | 73/861.05 |
| 4,355,638 | 10/1982 | Dwatschenko et al. .......... | 604/65 |
| 4,372,304 | 2/1983 | Avakian et al. .................. | 604/30 |
| 4,384,578 | 5/1983 | Winkler ........................... | 604/151 |
| 4,447,224 | 5/1984 | DeCant, Jr. et al. ........ | 128/DIG. 12 |
| 4,458,709 | 7/1984 | Springer .......................... | 73/861.95 |
| 4,483,200 | 11/1984 | Togawa et al. .................. | 73/861.95 |
| 4,532,811 | 8/1985 | Miller, Jr. et al. ............... | 73/861.95 |
| 4,613,327 | 9/1986 | Tegrarian et al. ................ | 604/141 |
| 4,680,445 | 7/1987 | Ogawa ............................. | 604/114 |
| 4,681,566 | 7/1987 | Fenton, Jr. et al. ........ | 128/DIG. 12 |
| 4,684,367 | 8/1987 | Schaffer et al. ............ | 128/DIG. 13 |
| 4,758,228 | 7/1988 | Williams ..................... | 128/DIG. 12 |
| 4,764,166 | 7/1988 | Spari ................................ | 604/65 |
| 4,778,450 | 10/1988 | Kamen ........................ | 128/DIG. 13 |
| 4,813,280 | 3/1989 | Miller, Jr. et al. ............... | 73/861.95 |

FOREIGN PATENT DOCUMENTS

| | | |
|---|---|---|
| 0023457 | 2/1981 | European Pat. Off. . |
| 2934565 | 3/1981 | Fed. Rep. of Germany ... 73/861.95 |
| 2441150 | 6/1980 | France . |
| 7402950 | 9/1975 | Netherlands ..................... 73/861.95 |
| 615769 | 1/1949 | United Kingdom . |
| 2037377A | 7/1990 | United Kingdom . |
| WO81/01658 | 6/1981 | World Int. Prop. O. . |

OTHER PUBLICATIONS

"Medical Instrumentation", John G. Webster, Houghton Mifflin Company, Boston, 1978, pp. 79-82, 95-96.

Primary Examiner—C. Fred Rosenbaum
Assistant Examiner—Mark Bockelman
Attorney, Agent, or Firm—Armstrong, Westerman, Hattori, McLeland & Naughton

[57] ABSTRACT

Medical infusion apparatus comprises a housing in which a standard flexible liquid reservoir is disposed. A constant-force spring applies pressure to the reservoir to force liquid out of the reservoir and along a conduit to a patient. The spring is energized by the opening of a lid of the housing which permits replacement of the reservoir.

The liquid flowing out of the reservoir passes through a molded conduit part which is configured so that it is positioned at a predetermined location with respect to a flow monitor. The flow monitor injects a pulse of heat, and detects the rate at which the heat pulse travels along the conduit. A microprocessor uses the sensed flow rate to control a stepper motor which regulates fluid flow by squeezing the conduit via a spring-biased member. The apparatus has active and standby modes in which the monitor is operated respectively more and less frequently.

25 Claims, 4 Drawing Sheets

MEDICAL INFUSION APPARATUS

This application is a continuation of Ser. No. 188,504 filed Apr. 29, 1988, and now abandoned.

This invention relates to medical infusion apparatus.

In general, there are currently two types of medical infusion apparatus. The first type is used for injecting very small doses of drugs into a patient over long periods. Such devices require very accurate control of a mechanism used to pressurise the liquid (e.g. a mechanism used to operate a syringe plunger), and the devices have to be arranged so that even very small variations from the set flow rate, which can be very dangerous, cannot occur. The devices are consequently designed only for very small flow rates, and are very expensive.

The present invention is concerned primarily with the other type of infusion apparatus, which is used for injecting relatively large quantities of liquid, e.g. saline, blood, etc. Although it is necessary for the flow to be carefully controlled, the very high degree of accuracy required for the first type of apparatus is not needed. The most common apparatus of the second type is the gravity-operated drip-feed. This apparatus comprises a stand from which is suspended a liquid reservoir, e.g. in the form of a bag of plastics material. Liquid is fed under gravity from the reservoir to the patient via a tube which is formed with a drip chamber. A clamp is provided downstream of the drip chamber, and can be adjusted so as to vary the flow restriction caused by the clamp, and thus vary the flow rate. The flow rate is estimated by counting the rate of drips in the drip chamber. This is an inexpensive arrangement, which is important especially for hospitals with a limited budget. However, there are a number of disadvantages. Setting up the apparatus is time consuming, and requires priming of the drip chamber which, if not done carefully, could result in problems such as air bubbles in the liquid being delivered to the patient. The apparatus is very clumsy, and makes movement of the patient awkward. The control of flow rate is very inaccurate, and this problem is exacerbated by the fact that it has to be checked regularly by a nurse. If the nurse is busy there can be fairly long periods between the checking of the apparatus. In the meantime, the cannula used to inject fluid into the patient could have shifted so that fluid is incorrectly being injected into tissue rather than, e.g. a vein. When the nurse does manage to check the apparatus, it takes several seconds at least to ensure that the flow rate is correct, and even longer if it is found that it needs adjustment.

In addition, although the cost of the apparatus as a whole is relatively low, the giving set, i.e. the tube leading from the reservoir to the patient and including the drip chamber and possibly a filter, is usually replaced after each usage, and therefore the cost of using the apparatus tends to be very high.

In some circumstances the apparatus is not sufficiently accurate. In these cases, the tendency is to use a peristaltic pump for liquid infusion. This gives highly accurate results, but is very expensive, and therefore few such devices are normally present in a hospital. The apparatus also requires significant amounts of power which makes transport difficult and, if battery-powered, requires that the apparatus be checked regularly to find out whether the batteries need replacement. The apparatus is arranged to deliver liquid using either a standard drip-feed giving set, thus encountering some of the problems mentioned above, or silicon tubing, which can be made to accurate dimensions but which is expensive.

Another known form of apparatus uses a sensor for counting drips and a regulator to control flow in response to the drip rate. This also has the problem of the drip chamber making the cost of usage high, and has a fairly high current consumption.

There have been various proposals for dealing with these problems, but they suffer to some extent from the disadvantages referred to, and have not met with commercial success.

U.S. Pat. No. 4,613,327 discloses a medical infusion apparatus which is said to be compact and portable and to produce little noise. It would, however, be desirable to provide apparatus in which these factors are considerably improved, in which the power requirements are substantially decreased, and in which it is ensured that liquid is administered to patients in the correct amounts.

In accordance with a first aspect of the invention there is provided a medical infusion apparatus comprising a housing for supporting a liquid reservoir and a conduit for delivering liquid from the reservoir to a position outside the housing, the housing also supporting means for applying pressure to the reservoir to cause liquid to flow along the conduit, means for sensing the flow of liquid along the conduit, and means responsive to the sensing means for regulating the flow. The housing preferably forms an enclosure within which the reservoir, the conduit, the pressurising means, the sensor, the regulator and a control circuit for the sensor and regulator are located. The enclosure preferably has an access member, such as a door or lid, which can be opened to permit replacement of the reservoir and/or conduit. As will be explained in more detail below, such an arrangement facilitates the provision of a self-contained and compact infusion apparatus which provides a properly controlled liquid flow.

An infusion apparatus according to the present invention is preferably electrically operated. However, it is very important that the apparatus consume very small amounts of current so that the apparatus can be made battery-operated and thus more portable, and preferably designed such that battery replacement is required only after relatively long periods of e.g. several months. It is desired that the current consumption be of the order of 3 mA at 6 volts, so that the apparatus can be powered for several months at least by small dry-cell batteries. Several aspects of the invention explained below are aimed at reducing the power consumption to such an order of magnitude, which has not previously been achieved in the type of medical infusion apparatus with which the present invention is concerned.

In accordance with one of these aspects, a medical infusion apparatus comprises a flexible reservoir for storing liquid, a conduit for delivering liquid from the reservoir to a patient, and resilient pressurising means which can be caused manually to store energy which is then used for applying pressure to the reservoir to cause liquid to flow from the reservoir along the conduit, the apparatus further comprising means for intermittently monitoring the flow rate, and a control circuit responsive to the monitoring means for regulating the rate.

Preferably, the resilient pressurising means comprises a spring acting upon the flexible reservoir. The spring preferably provides a substantially constant force, and may be a sheet of, e.g., steel which can be unwound from a rolled form (or rolled up) so that as it rewinds (or unrolls) it gradually squeezes liquid from the reservoir.

In the preferred embodiment, the apparatus has an enclosure such as that referred to above, and the opening of the access member of the enclosure withdraws the resilient pressurising means from the reservoir so as to facilitate the removal and replacement of the reservoir. Also, the opening of the access member preferably causes energy to be stored by the pressurising means. Preferably the closing of the access member causes the pressurising means to act against the reservoir.

In such an arrangement, power consumption is reduced by virtue of the type of pressurising means and by the intermittent monitoring of the flow rate. Preferably, the position of the regulator which determines the rate of flow of liquid from the apparatus is controlled by a motor, and is stable while the motor is de-energised. This further reduces power consumption by permitting a desired regulator position to be achieved by electrical control of the motor, while avoiding the need to maintain a supply of current to the regulating means in order to keep the regulator at the desired position. The motor may be an ordinary motor preferably coupled to the regulator by gears which produce a high gear ratio so that the pressure in the tube is insufficient to shift the regulator when the motor is de-energised. Alternatively, however, the motor may be a stepper motor.

Whenever the flow rate monitor determines that an alteration of the flow rate is required, the system is preferably arranged to drive the regulator using a signal which is determined by the amount by which the detected flow rate differs from the desired rate. This signal could for example control the amount of time for which the motor is operated, or the number of steps moved by the motor if this is a stepper motor. This is preferable to carrying out repeated incremental changes of regulator position, and each time checking the resulting altered flow rate, because the latter technique would require greater current consumption. However, if the interval between monitoring operations is relatively long in order to save power, it is important that the flow rate is corrected in a small number of stages. Accordingly, it is necessary for the response of the regulator to be reasonably predictable and repeatable.

It is also important that the regulator be designed so that the cost of use of the apparatus is not significantly increased. For this reason, it is preferred that the regulator be arranged to act upon a simple tube, such as the inexpensive P.V.C. tubes used in conventional giving sets. The regulator preferably squeezes the sides of the tube together and thereby controls the rate of flow.

Regulators of this type are disclosed in U.S. Pat. Nos. 3,543,752 and 4,372,304. In the former patent, plastic tubing is positioned between a regulator member and a rigid stationary base, and the regulator member is spring biased against the plastic tubing in order to close it. The regulator member can be shifted against the spring bias in order to open the tubing. The regulator is merely required to open and close the tubing. In U.S. Pat. No. 4,372,304, a stepper motor operates on a plunger via reduction gearing in order to cause axial movement of the plunger to squeeze a tube. In both these cases, it would be extremely difficult to achieve controllable flow rates with a predictable and repeatable response as is required for relatively infrequent adjustment of the regulator.

In accordance with another aspect of the invention, there is provided medical infusion apparatus comprising a regulator the position of which can be adjusted in order to regulate the flow of liquid from the apparatus, the regulator comprising first and second members between which can be located a conduit carrying the liquid, the first and second members being movable toward each other in order to restrict liquid flow, and at least one of the members being resiliently biassed toward the other member. It has been found that by resiliently biassing one of the members, rather than having it fixed in position, the range of operation of the regulator which corresponds to the range of flow rates over which control is to be exercised is substantially increased, and the predictability and repeatability of the regulator response is substantially increased, without requiring special tubing. The consequence of this is that accurate alteration of the flow rate is more easily achieved, and by proper arrangement of the device a more linear control can be obtained. The conduit may be a simple tube, e.g. made of P.V.C.

Preferably, the arrangement is such that the tube is caused to adopt a substantially "U"-shaped configuration, with the first and second members engaging opposite sides of the tube at the base of the "U", and further members engaging the tube at respective sides of the base of the "U". Such an arrangement facilitates the complete shutting-off of the liquid flow, which is desired in certain circumstances.

A regulator of the above type has the further advantage that, despite manufacturing irregularities in both the infusion apparatus and the conduit, the predictability of the regulator operation is such that it is possible to ensure that a particular setting of the regulator upon start-up will result in an intermediate flow rate which permits monitoring but is not excessive for the patient.

It is desirable for the flow monitor of the apparatus to be inexpensive and accurate, and to have a low power consumption. Known flow monitors for infusion apparatus include drop sensors, such as that shown in WO 86/03415. These need to operate continuously and therefore consume large amounts of current. They also increase the cost of the disposable parts of the apparatus, because of the provision of a drip chamber, resulting in very high usage costs. Another flow sensor is disclosed in U.S. Pat. No. 4,384,578. The sensor disclosed here employs tubing which has spaced-apart tubular metal segments, the temperatures of which are sensed by thermistors. A resistor is provided to apply heat to the downstream segment. The current required to maintain a constant temperature differential is measured, and used as an indication of fluid flow. Such an arrangement also requires large amounts of current, is of low accuracy, and is affected by ambient temperatures so that thermal insulation of parts of the apparatus is required. In addition, the disposable part of the apparatus needs to include two separate metal segments forming part of the sensor.

According to a further aspect of the present invention, a monitor for monitoring the flow rate of liquid along conduit in a medical infusion apparatus comprises means for applying a pulse of heat to liquid in the conduit, and means downstream of the location at which the heat pulse is applied for sensing a temperature change in the liquid passing along the conduit. In effect, the speed at which the heat pulse travels down the conduit is detected in order to determine the flow rate. This aspect of the invention can be embodied in various forms. For example, the time between the injection of the heat pulse and the sensing of the heat pulse having reached a predetermined position downstream can be monitored. Alternatively, the speed at which the heat pulse passes the sensing point can be monitored. In the preferred embodiment, however, instead of just one sensor there are two sensors downstream of the location at which the heat pulse is injected, and the time taken for the heat pulse to travel between the two sensors is monitored to give an indication of flow rate. This results in the measurement being independent of the time required for the initial heating of the liquid, which depends on factors which may vary.

The advantages of this aspect of the invention include the fact that the sensor can be made non-intrusive, so that the conduit is readily removable from the monitor and so as to reduce the possibility of contamination of the liquid. It may also be designed so that it requires very small amounts of current in operation, and needs to be operated only at relatively long intervals.

The heat pulse can be injected using a flexible resistive material disposed around the conduit and intermittently powered to generate heat. The material is preferably resilient, and may serve as a clip for retaining the conduit in position, and thus ensuring its close proximity to the heat source. The sensors are preferably responsive to infra-red radiation emitted by the liquid in the conduit.

In accordance with a still further aspect of the invention, a medical infusion apparatus includes a conduit for delivering liquid from a reservoir to a patient, at least part of the conduit preferably being an integrally formed member and being carried by but detachable from a housing of the apparatus, the conduit part and a support arrangement of the housing being configured such that in use they interengage to locate the conduit part at a predetermined location with respect to a fluid flow monitor of the apparatus. Preferably the conduit part is transparent to infra-red radiation and is located in proximity to at least one infra-red sensor of the monitor. Preferably the support arrangement includes a heat-generating member serving as both part of the flow monitor and a locating means for the conduit part. Preferably the conduit part has a portion adapted for insertion into the reservoir. Such an arrangement permits the use of inexpensive conduits which do not have any built-in means for indicating flow rate but nevertheless ensure that the apparatus as a whole can monitor the flow rate accurately. Making the conduit inexpensive is very important as it is a part of the apparatus that is discarded after use. U.S. Pat. No. 4,384,578 also discloses a conduit having a part locatable at a predetermined position in the housing of a flow sensor. However, the part needs to include two metal segments with an intermediate piece of plastics tubing, and is remote from the reservoir.

Another independent aspect of the invention is directed to the further reduction of the current required by a flow monitor. In accordance with this aspect, a flow rate monitor for a medical infusion apparatus is arranged to operate periodically, so that the flow rate is monitored at predetermined intervals, the monitor having at least an active mode and a standby mode, the intervals between monitoring being shorter in the active mode than in the standby mode. The periodic operation of the sensor reduces the total current consumption. By having two modes of operation, it is possible to ensure that the flow rate is closely monitored at critical times, such as immediately after the apparatus is put into operation, while enabling greater reduction in current consumption during non-critical periods.

Preferably the monitor is actuated using a microprocessor forming part of a control circuit of the apparatus. The microprocessor preferably itself has active and standby modes in which it consumes respectively greater and smaller amounts of current. A timer may be provided for generating, at predetermined intervals, signals for causing the microprocessor to enter its active mode.

The use of a microprocessor control circuit incorporating a microprocessor having two modes of operation, one of which results in a smaller current consumption, is considered a separate aspect of the invention. Preferably, the apparatus is arranged to detect one or both of the following conditions, in response to which the microprocessor is caused to enter its active mode: (a) a signal from a timer, as indicated above, to enable monitoring (and if necessary regulation) of the flow rate, and (b) a signal from a sensor detecting excessive amounts of air passing along the conduit so that the microprocessor can, for example, generate an alarm.

It will be apparent from the foregoing and the following that the invention has a number of independently advantageous aspects which can be used separately, but which in the preferred embodiment are combined to form a device which at least substantially mitigates the problems referred to above. The apparatus is both less expensive to use than conventional equipment and provides better control. The extremely low current consumption also results in extremely portable equipment which requires little attention.

An arrangement according to the invention will now be described by way of example with reference to the accompanying drawings, in which.

Figure 4:
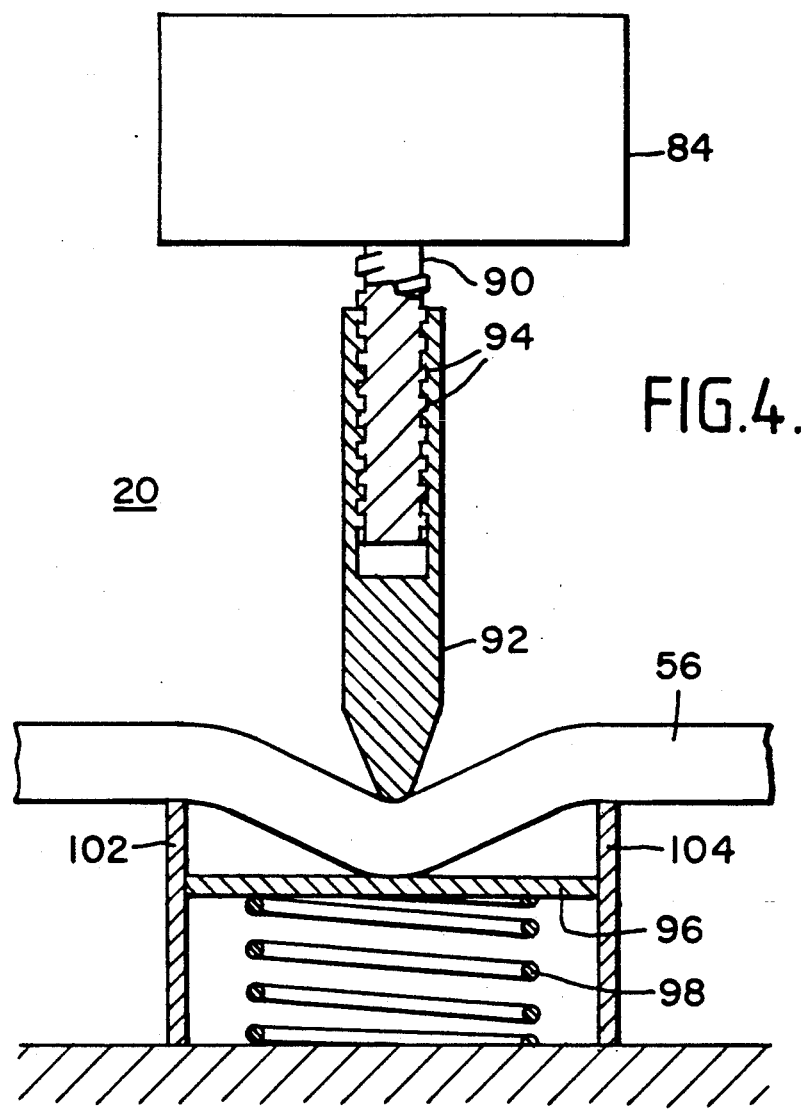

FIG. 4 schematically illustrates a flow rate regulator of the apparatus; and

Figure 5:
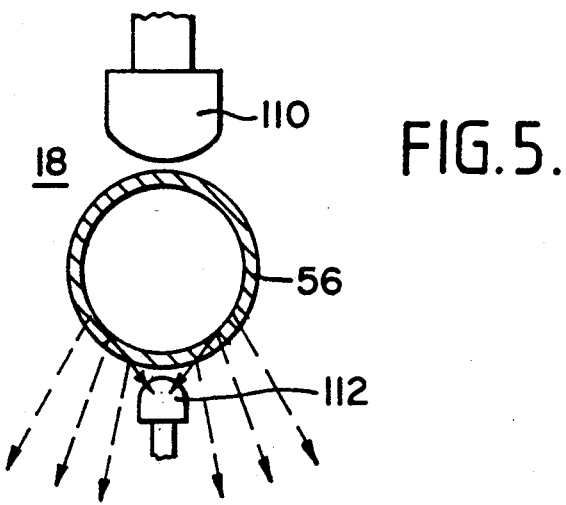

FIG. 5 schematically illustrates a bubble detector of the apparatus.

Figure 1:
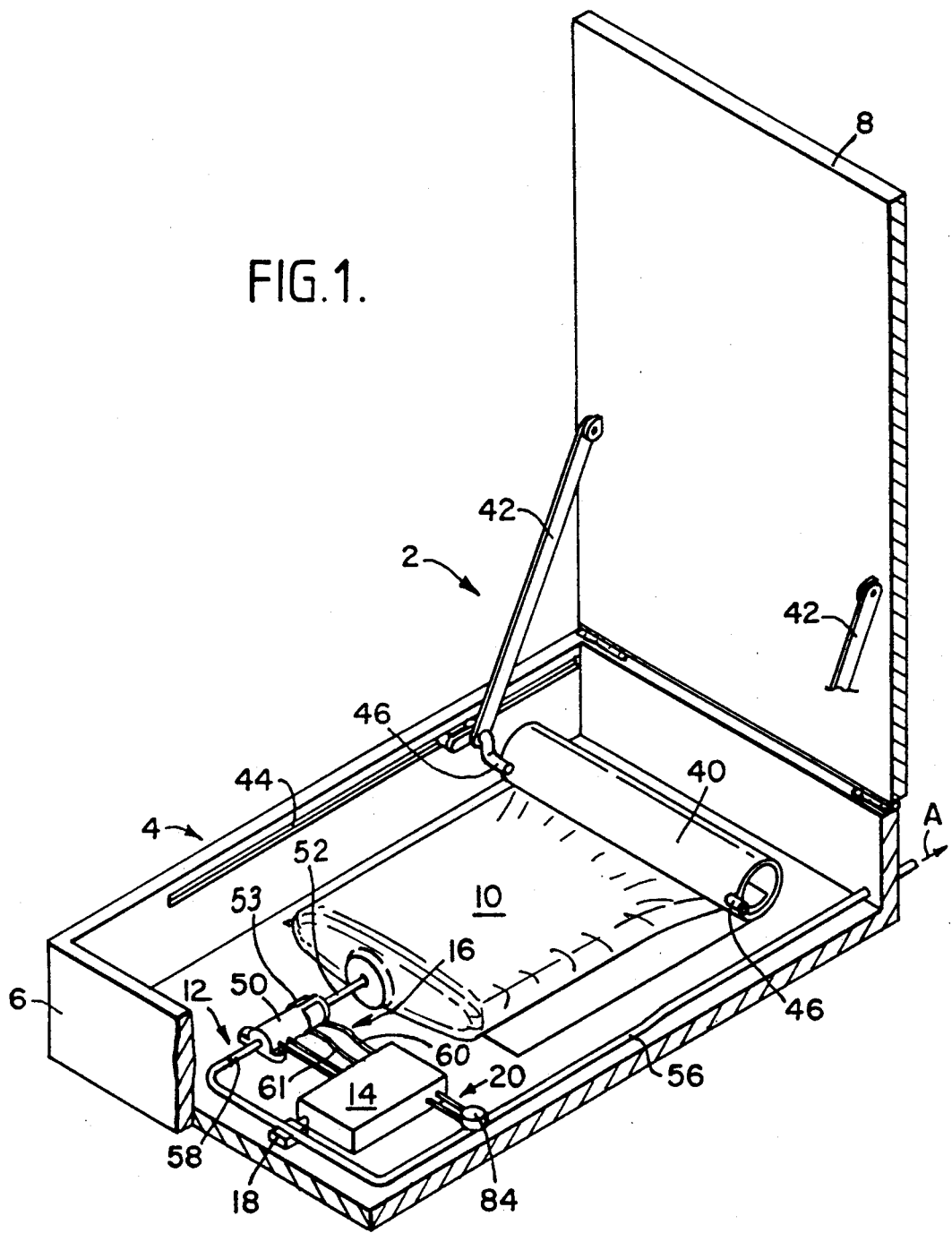
FIG. 1 is a perspective view, partly cut away, schematically showing a medical infusion apparatus according to the invention.
Figure 2:
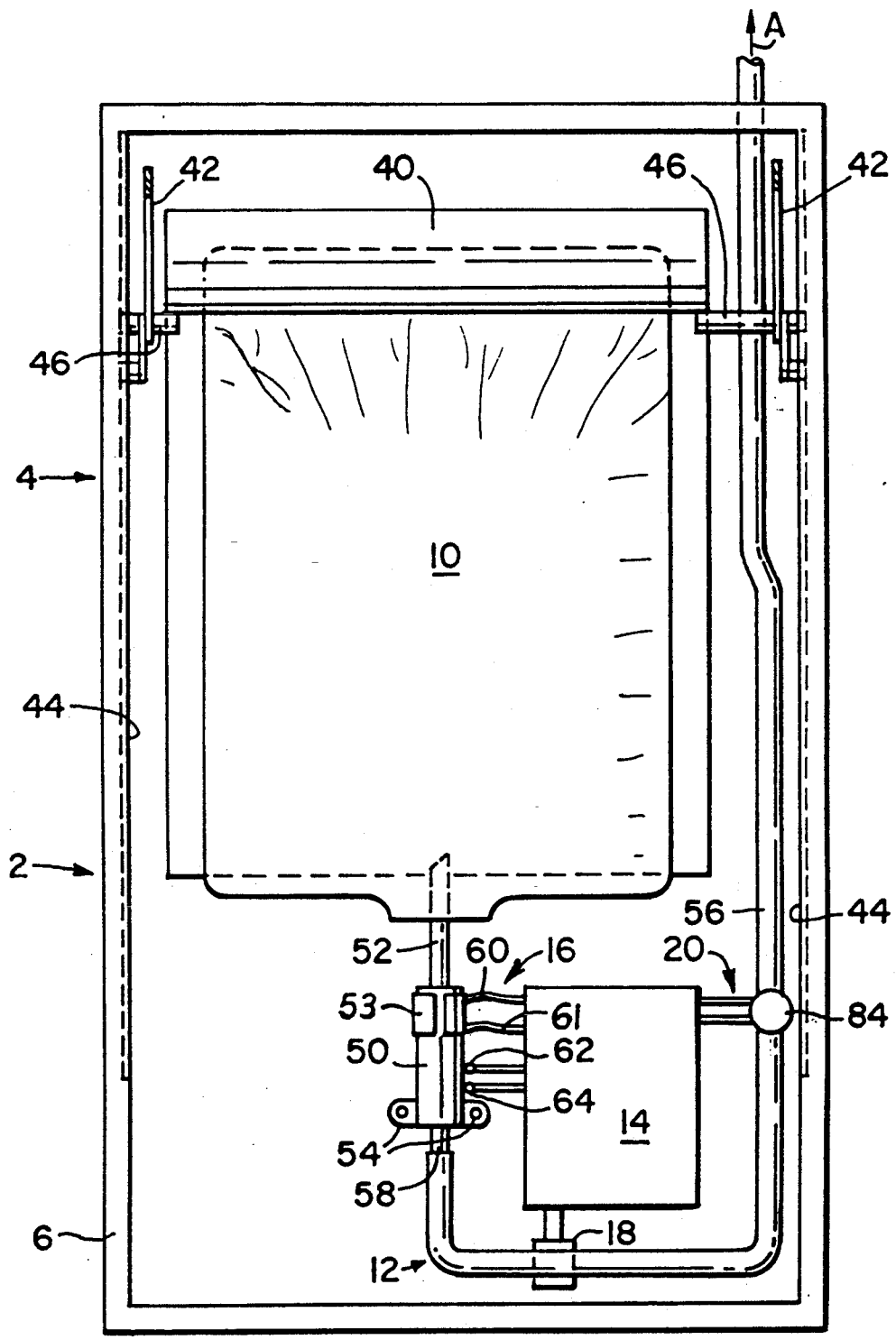
FIG. 2 is a plan view of the apparatus of FIG. 1.

Referring to FIGS. 1 and 2, the apparatus 2 comprises a housing 4 having a base 6 and a hinged lid 8. The housing base 6 supports a reservoir 10 in the form of a flexible plastics bag of a standard type used in drip feed apparatus, and a conduit indicated generally at 12 which conveys liquid from the reservoir 10 in the direction of arrow A to a patient.

The housing base 6 also supports a control unit 14 coupled to a sensor arrangement 16, a bubble detector 18 and a flow rate regulator 20. In addition, the housing 4 has an externally-visible digital display, externally-visible warning lights, externally-operable controls, preferably in the form of a keyboard, and a sound transducer for emitting alarm sounds. These devices are not shown in FIGS. 1 and 2, but are indicated schematically in FIG. 3 and are of types known per se for microprocessor-controlled appliances.

The base 6 also supports a spring 40 used to pressurise the reservoir 10. The spring comprises a steel sheet in a rolled configuration, and is shown in FIGS. 1 and 2 in a state in which it is substantially unrolled so that the reservoir 10 can be removed. In use, the spring 40 tends to roll up and thereby squeeze fluid from the reservoir 10.

The lid 8 has a pair of arms 42 hinged thereto at their upper ends. The lower ends are guided for movement substantially in the direction in which the spring 40 rolls and unrolls by slots 44. Extensions 46 fixed to the lower ends of the arms 42 are arranged to engage the spring 40 so that as the lid 8 is opened the spring 40 is caused to unroll. This supplies energy to the spring 40, and also moves it to the position in which the reservoir 10 can be removed. When the lid 8 is closed, the spring 40 is able to start rolling up and thus pressurising the reservoir 10. If desired, a latch could be provided to hold the lid 8 in its open position.

The spring 40 is of a type which tends to exert a constant force as it rolls up.

The conduit 12 includes a part 50 which is formed of a unitary molding. The part 50 is generally tubular and has an inlet end 52 forming a spike which is pointed so that it can be inserted in the usual way into the standard reservoir 10. The part 50 is fitted into a resilient "C"-shaped clip 53 fixed to the base 6 of the housing 4, which holds the part 50 in position. If desired, the central section of the part 50 may have flanges indicated at 54 with apertures for locating on pegs fixed to the base 6 of the housing 4. In any event, the part 50 is positioned in a predetermined location with respect to the sensor arrangement 16. The remainder of the conduit 12 comprises a simple tube 56 made of P.V.C. which is pushed onto the outlet end 58 of the part 50 and which extends past the bubble detector 18, the regulator 20 and then out of the housing 4.

Because the conduit 12 comprises a simple tube 56 and a molded part 50 (together with an in-line filter e.g. between the part 50 and the tube 56, if desired), the conduit is substantially less expensive than the conventional "giving sets" used in standard gravity-operated drip-feed apparatus, as a result of the fact that the disposable conduit need not include a drip-feed chamber, or an individual regulator. The part 50 is used both for insertion into the reservoir and, as explained below, enabling sensing of flow rate. It will be appreciated that even a small saving on the disposable parts of the apparatus quickly justifies the capital expense of the apparatus as a whole and thereafter results in very substantial cost savings.

The sensor arrangement 16 comprises a heat source formed by the clip 53 which is made of electrically resistive material, preferably hard wearing, such as cermet. This is connected to the control unit 14 by leads 60,61 so that electrical power can be applied to heat up the clip 53 and hence the liquid in the conduit part 50. The sensor arrangement 16 also comprises two pyroelectric sensors 62 and 64 (Mullard type No. RPY 100). Other sensors could be used, but passive infra-red sensors are preferred. The source 53 is, in use, energised for a brief period in order to heat up, by a very small amount, the liquid flowing through the conduit 12. This is then detected by the sensors 62 and 64. For this purpose, the material of the part 50 of the conduit 12 is selected so that it is substantially transparent to infra-red radiation. The material may for example be polyethylene. After the source 53 has been briefly energised, the output signals from the sensors 62 and 64 are checked. This can be done in a variety of ways. For example, the time between the occurrence of the peaks in the signals from the sensors can be measured, or alternatively the point at which the value of each output signal increases to a predetermined proportion (e.g. 80%) of its peak value can be measured, and the time between these points determined. The latter can be achieved by repeatedly sampling the outputs of the sensors 62 and 64, storing the samples, determining therefrom when the peak has been reached, and then determining the time at which the samples representing the predetermined proportion of the peak were taken. In any event, a value indicative of the rate at which fluid flows along the conduit is derived. This can if desired be converted into a measurement of flow, by for example using the derived value to select a location in a table stored in a memory of the control circuit, which table contains corresponding flow rate values. If the flow rate deviates from a selected rate, the control unit 14 operates regulator 20 in order to increase or decrease the flow rate, as appropriate.

The regulator 20 is shown schematically in FIG. 4. The regulator comprises a stepper motor 84 having an output shaft 90 which co-operates with a regulating member 92 by means of a helical thread 94, so that rotary movement of the shaft 90 is converted into linear movement of the member 92, in an upward/downward direction as shown in FIG. 4.

The tube 56 passes between the regulating member 92 and an opposing member 96 which is biassed by a spring 98 toward the regulating member 92. The opposing member 96 engages the tube 56 at a point opposite that at which it is engaged by the regulating member 92. The total compression is thus determined by the position of regulating member 92 and the force of spring 98. This gives rise to the extended operating range of the regulator and the advantages mentioned above. Instead of or in addition to the spring 98, the member 92 could be replaced by a first member driven by the motor, and a second member pressed against the tube 56 by the first member via a spring.

Further members 102 and 104, which are fixedly positioned, engage the tube 56 at opposite sides of the point at which it is squeezed, so that the tube 56 adopts a substantially "U"-shaped configuration. Operation of the stepper motor 84 causes the regulating member 92 to move toward or away from the opposing member 96, thus varying the amount by which the tube 56 is pinched, and therefore varying the restriction to liquid flow. By having the tube in a "U"-shaped configuration, which gradually deepens as the flow is restricted, the tube can be more readily pinched to a sufficient extent as to shut-off the liquid flow.

The bubble detector 18 is shown in FIG. 5. This comprises a radiation source 110, which could be a lamp, an LED, a source of infra-red radiation, etc. The source 110 is positioned on the opposite side of the tube 56 from a radiation sensor 112, which is arranged to detect radiation only in the central region of the tube.

The tube, which is made of transparent plastics material such as P.V.C., has parallel inner and outer walls. In the absence of liquid in the tube 56, radiation from the source 110 passes substantially straight through the tube 56, and leaves the tube in a wide variety of directions as indicated by the arrows shown in phantom. The radiation is generally diffuse, and little reaches the sensor 112.

However, when liquid is in the tube 56, it acts as a lens and focusses the radiation onto the sensor 112 as shown by the solid-line arrows. This results in an increase in the detected intensity. Air bubbles can thus be detected by looking for decreases in sensed radiation intensity.

Depending upon the wavelength of the radiation, there may be some liquids, e.g. blood, which have an optical density such that air bubbles result in an increase in the sensed radiation. In this case, the circuit is arranged to detect either increases or decreases in the sensed radiation and in response thereto to provide a signal indicating the presence of an air bubble. The circuit could be arranged to store an indication of the type of liquid being supplied (which could for example be entered using the keyboard), and to detect only decreases or only increases in sensed radiation depending upon the liquid type.

If desired, the bubble detector 18 could be positioned to detect air bubbles passing through the part 50 of the conduit 12, rather than the tube 56.

The sensor 18 may alternatively comprise a pair of capacitor plates positioned on respective sides of the tube 56. If an air bubble flows along the tube, the capacitance of the detector 18 will alter as the bubble passes between the plates. This can be detected, and if the change in capacitance lasts sufficiently long an alarm signal can be generated.

It should be noted that the part 50 can be configured, e.g. with recesses, to permit the sensor arrangement 16 and/or the bubble detector 18 to be fitted thereto in a predetermined location, rather than relying on all the elements being located accurately with respect to the base 6 of the housing 4.

Figure 3:
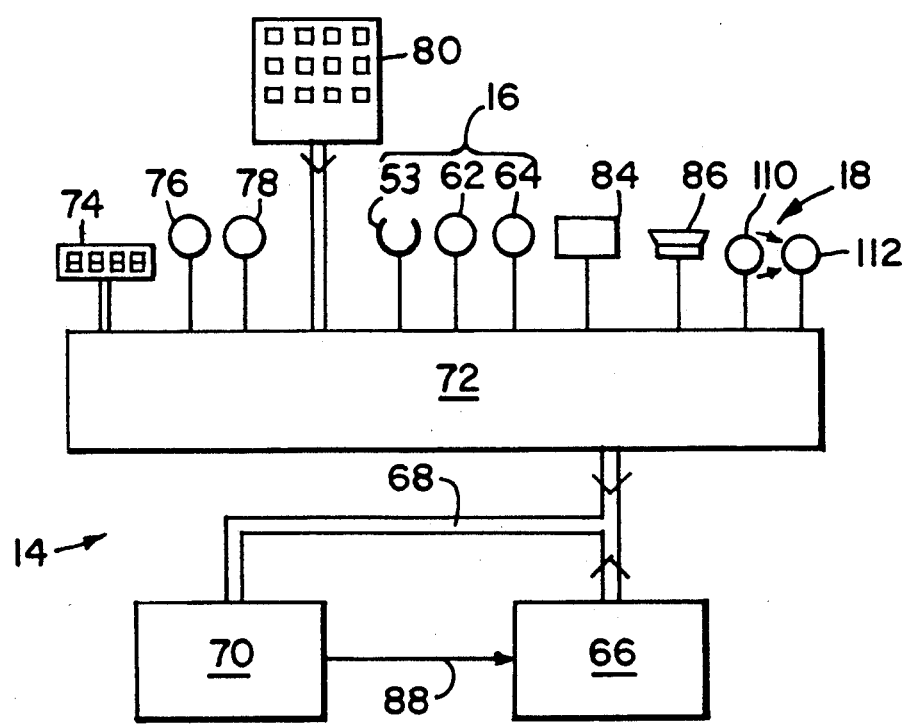
FIG. 3 is a schematic diagram of the circuit of the apparatus.

The arrangement described above is controlled by a control unit 14 shown in FIG. 3. The control unit 14 comprises a microprocessor 66, e.g. type 80C48 supplied by Intel, having an input/output bus 68 coupled to a programmable timer or counter 70 operable to generate output signals at regular intervals. The bus 68 is also coupled, via appropriate interface circuitry 72, to a digital display 74, warning lights 76 and 78, a keyboard 80, the stepper motor 84 an audio transducer 86, the heat source 53, the sensors 62 and 64, and the bubble detector 18.

The apparatus may be arranged to operate as follows. After the apparatus has been turned on by a switch of the keyboard 80, or automatically by the closing of the lid 8 with a reservoir 10 in position, the microprocessor 66 begins to operate in an active mode. The microprocessor detects the operating of keys of the keyboard 80, so that the user can enter a digital value representative of desired flow rate, which is displayed on the display 74. The microprocessor causes the source 53 to be pulsed, and detects the flow rate using the signals from sensor 62 and 64. If this differs from that set by the keyboard 80, the microprocessor generates a signal to cause the motor 84 to shift the position of the regulating member 92 either to increase or decrease the flow rate by an amount depending upon the variation of the flow rate from the set rate. The microprocessor again detects the flow rate using the source 53 and sensors 62 and 64, and continues to operate the motor 84 until the flow rate is close to the set rate. Due to the fact that the time taken for a sensing operation may vary considerably with different flow rates, the time between successive sensing operations may, for example, be of the order of one minute.

The microprocessor 66 then sends a counter set value along bus 68 to the counter 70. The microprocessor then switches into a standby mode, during which it consumes a relatively small amount of current. The counter 70 continues to operate during this period. The set value is continuously decremented, and when it reaches zero a signal is output on a line 88 to cause the microprocessor to enter its active mode. At this point the source 53 is energised and the outputs from sensors 62 and 64 checked to determine the flow rate. If this has departed from the set value, the motor 84 is again energised to alter the flow regulation by an amount dependent on the detected variation. The count value is again delivered to the counter 70 and the standby mode entered. However, if the departure from the set rate exceeds a predetermined amount, the microprocessor instead remains in its active mode so that regulation is carried out more rapidly.

The circuit 72 includes components for regularly checking the output from the bubble detector 18. At regular intervals, e.g. for 10 $\mu$s each millisecond, the source 110 is activated and the output from the sensor 112 checked by a comparator. If the output level is low, an interrupt signal is produced to put the microprocessor into its active mode. The warning lamp 76 is then illuminated. An audible alarm is also sounded, using the audio transducer 86. This arrangement could be modified so that the signal for placing the microprocessor in its active mode, or the signals generated to actuate the warning lamp 76 and audio transducer 86, are produced only if the size of the air bubble exceeds a predetermined size.

Whenever the microprocessor enters its active mode it checks the flow rate. If this is substantially different from the set rate and cannot quickly be corrected by operation of the regulator, the warning light 78 is operated and the alarm sounded, because this may be an indication that the liquid leaving the infusion apparatus is not being properly delivered to the patient.

The above arrangement may be modified so that the circuit 72 continually checks the output of the sensor arrangement 16, this circuit causing the microprocessor to enter its active mode upon detecting that an alarm needs to be given. The circuit may instead operate periodically, in response to a timer. In this arrangement, the microprocessor becomes active if an alarm is to be given or if a signal is output from counter 70, but alternatively the microprocessor can be caused to enter its active state only when an alarm needs to be given or the flow rate needs to be adjusted. This would avoid the need for a counter 70 to cause the microprocessor to enter its active mode.

The microprocessor 66 monitors the total amount of liquid delivered to the patient. This can be achieved by digitally integrating the detected flow rate with time. The microprocessor 66 is preferably capable of causing the total amount of liquid delivered by the apparatus to be displayed on the display 74, and/or permitting a user to set a permitted volume using the keyboard 80, following delivery of which the microprocessor 66 automatically shuts-off further liquid flow. In addition, the microprocessor 66 preferably gives an indication when the detected volume approaches the total volume initially stored in the reservoir, so as to indicate that replacement of the reservoir is required.

Various modifications to the system are possible. For example, instead of using the heat source 53, a microwave energy source could be used, or the part 50 could incorporate a conductor in which eddy currents are generated to heat the liquid. The heat need not be applied to the liquid in the part 50. Instead of using heat for monitoring flow, it would be possible to apply pressure vibrations and measure the difference in phase of the vibrations as sensed at points equidistant from the source. It would also be possible to measure the rate at which the temperature of the liquid rises or falls as a result of injection of a heat pulse, as this would be determined by flow rate. There may be occasions on which it is desired to inject simultaneously more than one type of liquid, and for this purpose the housing 4 may be provided with an inlet for receiving the output flow from a similar apparatus, the inlet directing this flow into the conduit 12. Alternatively, the housing 4 may be designed to support two reservoirs, and have a respective sensor arrangement 16, regulator 20 and, if desired, bubble detector 18 for each of the reservoirs. These could all be coupled to the same control unit 14. The conduits 56 would then be linked at a point downstream of the regulators.

Although the above preferred embodiment uses a mechanical spring for pressurising the reservoir, it will be appreciated that many of the advantages can still be achieved if the apparatus is modified so that liquid flow is produced by gravity.

We claim:

1. Medical infusion apparatus comprising:
a liquid reservoir;
a conduit for delivering liquid from the reservoir to a patient; and
a monitor for monitoring the flow rate of said liquid along said conduit, said monitor comprising means external of said conduit for applying a pulse of heat to a liquid at a location in the conduit, and radiation sensing means outside a periphery of the conduit including an infra-red sensor spaced from said conduit for sensing a change in temperature of liquid at a position downstream of the location, so that the speed of travel of the heat pulse can be determined in response to radiation sensed by the sensor;
whereby the monitor is non-intrusive to permit removal of the conduit from the monitor.

2. Medical infusion apparatus comprising:
a liquid reservoir;
a conduit for delivering liquid from the reservoir to a patient;
a monitor for monitoring the flow rate of said liquid along said conduit, said monitor comprising means external of said conduit for applying a pulse of heat to liquid at a location in the conduit and radiation sensing means outside a periphery of the conduit including an infra-red sensor spaced from said conduit for sensing a change in temperature of liquid at a position downstream of the location, so that the speed of travel of the heat pulse can be determined in response to radiation sensed by the sensor;
whereby the monitor is non-intrusive to permit removal of the conduit from the monitor;
the apparatus further comprising a regulator having an adjustable position for regulating the flow of liquid from the reservoir, and a motor which can be energized to adjust said regulator position, the regulator position being stable while the motor is de-energized.

3. Medical infusion apparatus comprising:
a liquid reservoir;
a conduit for delivering liquid from the reservoir to a patient;
a monitor for monitoring the flow rate of said liquid along said conduit, said monitor comprising means external of said conduit for applying a pulse of heat to liquid at a location in the conduit and radiation sensing means outside a periphery of the conduit including an infra-red sensor spaced from said conduit for sensing a change in temperature of liquid at a position downstream of the location, so that the speed of travel of the heat pulse can be determined in response to radiation sensed by the sensor;
whereby the monitor is non-intrusive to permit removal of the conduit from the monitor;
said apparatus further comprising pressurizing means for applying pressure to the reservoir to cause liquid to flow along the conduit, regulating means for regulating the flow in response to said monitor, and a housing, said housing supporting said reservoir, said conduit, said monitor, said pressurizing means and said regulating means.

4. Apparatus as claimed in claim 1, 2 or 3, said radiation sensing means comprising first and second infra-red sensors for sensing temperature changes at two positions spaced along the length of the conduit, whereby the time taken for the heat pulse to pass from said first position to said second position can be determined.

5. Apparatus as claimed in claim 1, 2 or 3, wherein said means for applying a pulse of heat comprises a member of resistive material in proximity to the conduit.

6. Apparatus as claimed in claim 1, 2 or 3, wherein said means for applying a pulse of heat is in resilient engagement with said conduit.

7. Apparatus as claimed in claim 1, 2 or 3, said apparatus further comprising control means for intermittently operating the monitor at predetermined intervals.

8. Apparatus as claimed in claim 7, wherein said control means has first and second operational modes, said predetermined intervals being shorter in said first operational mode than in said second operational mode.

9. Apparatus as claimed in claim 1, 2 or 3, further comprising resilient pressurizing means which can be manually caused to store energy which is then used for applying pressure to said reservoir to cause liquid to flow from said reservoir along said conduit.

10. Apparatus as claimed in claim 9, further comprising an enclosure containing said reservoir, said enclosure having an access member which can be opened to permit access for removal of the reservoir, means being provided for withdrawing the resilient pressurizing means from the reservoir in response to opening of said access member, so as to facilitate the removal of the reservoir from said enclosure.

11. Apparatus as claimed in claim 10, wherein said withdrawing means is arranged to cause energy to be stored by said pressurizing means during withdrawal thereof.

12. Medical infusion apparatus comprising:
a liquid reservoir;
a conduit for delivering liquid from the reservoir to a patient;
a flow monitor for monitoring the rate of flow of liquid along the conduit, said monitor comprising means external of said conduit for applying a pulse of heat to liquid at a location in the conduit and radiation sensing means outside a periphery of said conduit including an infrared sensor spaced from said conduit for sensing a change in temperature of liquid at a position downstream of the location so that the speed of travel of the heat pulse can be determined in response to radiation sensed by the sensor; and
support means for supporting said conduit and said flow monitor;

said conduit comprising a unitary, integrally-formed insertion member having first and second portions, said first portion being adapted for insertion into said reservoir; and said insertion member being removable from said support means and said sensing means, and being configured such that, when carried by said support means, said second portion of said insertion member is located in a predetermined position with respect to the flow monitor, whereby the flow monitor can monitor the rate of flow of liquid through said second portion.

13. Apparatus as claimed in claim 12, wherein said insertion member is formed of material which is substantially transparent to infra-red radiation, said flow monitor comprising means external of said insertion member for applying heat to liquid flowing through said insertion member, and means external of said insertion member for sensing a change in the temperature of the liquid in said insertion member at a position downstream of the location at which the heat is applied.

14. Apparatus as claimed in claim 13, said radiation sensing means comprising first and second infra-red sensors for sensing temperature changes at two positions spaced along the length of the insertion member, whereby the time taken for the heat pulse to pass from said first position to said second position can be determined.

15. Apparatus as claimed in claim 13, wherein said means for applying heat comprises a member of resistive material in proximity to the insertion member.

16. Apparatus as claimed in claim 13, wherein said means for applying heat is in resilient engagement with said insertion member.

17. Apparatus as claimed in claim 12, said apparatus further comprising control means for intermittently operating the flow monitor at predetermined intervals.

18. Apparatus as claimed in claim 17, wherein said control means has first and second operational modes, said predetermined intervals being shorter in said first operational mode than in said second operational mode.

19. Apparatus as claimed in claim 12, further comprising resilient pressurizing means which can be manually caused to store energy which is then used for applying pressure to said reservoir to cause liquid to flow from said reservoir along said conduit.

20. Apparatus as claimed in claim 19, further comprising an enclosure containing said reservoir, said enclosure having an access member which can be opened to permit access for removal of the reservoir, means being provided for withdrawing the resilient pressurizing means from the reservoir in response to opening of said access member, so as to facilitate the removal of the reservoir from said enclosure.

21. Apparatus as claimed in claim 20, wherein said withdrawing means is arranged to cause energy to be stored by said pressurizing means during withdrawal thereof.

22. Apparatus as claimed in claim 12, the apparatus further comprising a regulator having an adjustable position for regulating the flow of liquid from the reservoir, and a motor which can be energized to adjust said regulator position, the regulator position being stable while the motor is de-energized.

23. Apparatus as claimed in claim 12, said apparatus further comprising pressurizing means for applying pressure to the reservoir to cause liquid to flow along the conduit, regulating means for regulating the flow in response to said monitor, and a housing, said housing supporting said reservoir, said conduit, said monitor, said pressurizing means and said regulating means.

24. Apparatus as claimed in claim 12 or 13, wherein said support means is also adapted to support said reservoir.

25. Medical infusion apparatus comprising:
a liquid reservoir;
a conduit for delivering liquid from the reservoir to a patient;
a flow rate monitor for monitoring the rate of flow of liquid from the reservoir to the patient;
control means for intermittently operating the flow rate monitor at predetermined intervals, said control means having first and second operational modes, said predetermined intervals being shorter during the first operational mode than during the second operations mode; and
a flow rate regulator for regulating the flow rate; said control means having an output for controlling said flow rate regulator, said control means comprising a microprocessor performing processing apparatus in said active mode, and said microprocessor consuming less current in the standby mode than in the active mode, wherein said microprocessor is arranged to be in its active mode during said first operational mode of said control means, and is caused to enter its standby mode when the control means is in its second operational mode, the control means further including means operable during said second operational mode to cause the microprocessor to enter its active mode in response either to a lapsing of a predetermined interval or to detection of a disturbance in the flow of liquid, so that the microprocessor can then determine and if necessary regulate the flow rate,
further including means for sensing disturbances in the flow of liquid caused by the appearance of air bubbles in order to cause the microprocessor to enter its active mode.

* * * * *